(12) United States Patent
Mikochik et al.

(10) Patent No.: US 9,108,940 B2
(45) Date of Patent: *Aug. 18, 2015

(54) CONVERSION OF 5-(CHLOROMETHYL)-2-FURALDEHYDE INTO 5-METHYL-2-FUROIC ACID AND DERIVATIVES THEREOF

(71) Applicants: Peter Mikochik, Groton, CT (US); Aviad Cahana, Albuquerque, NM (US)

(72) Inventors: Peter Mikochik, Groton, CT (US); Aviad Cahana, Albuquerque, NM (US)

(73) Assignee: XF TECHNOLOGIES INC., Albuquerque, NM (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/192,828

(22) Filed: Feb. 27, 2014

(65) Prior Publication Data

US 2014/0194633 A1    Jul. 10, 2014

Related U.S. Application Data

(63) Continuation of application No. 13/817,452, filed as application No. PCT/US2011/048009 on Aug. 17, 2011, now Pat. No. 8,710,250.

(60) Provisional application No. 61/375,189, filed on Aug. 19, 2010, provisional application No. 61/375,367, filed on Aug. 20, 2010.

(51) Int. Cl.
     *C07D 307/02*      (2006.01)
     *C07D 307/68*      (2006.01)

(52) U.S. Cl.
     CPC .................................. *C07D 307/68* (2013.01)

(58) Field of Classification Search
     CPC ....................................................... C07D 307/68
     USPC ......................................................... 549/484
     See application file for complete search history.

(56) References Cited

U.S. PATENT DOCUMENTS 8,710,250 B2 *    4/2014    Mikochik et al. ............. 549/484

* cited by examiner

*Primary Examiner* — T. Victor Oh
(74) *Attorney, Agent, or Firm* — V. Gerald Grafe

(57) ABSTRACT

The present invention concerns the synthesis of 5-methyl-2-furoic acid, including ester, amide, and thioester derivatives of such from 5-(chloromethyl)-2-furaldehyde (CMF). The molecules so prepared are useful as intermediates for pharmaceutical, food, and fragrance molecules; as well as fuel or fuel additives.

13 Claims, 9 Drawing Sheets

Chloromethyl fufural (CMF)

Hydroxymethyl fufural (HMF)

Furan

Glucose

CONVERSION OF 5-(CHLOROMETHYL)-2-FURALDEHYDE INTO 5-METHYL-2-FUROIC ACID AND DERIVATIVES THEREOF

CROSS REFERENCE TO RELATED APPLICATIONS AND TECHNICAL FIELD

This application claims priority as a continuation of U.S. Ser. No. 13/817,452, filed Mar. 5, 2013; and thence to its priority applications; U.S. Ser. No. 13/817,452 was a 371 of PCT/US11/48009, filed Aug. 17, 2011; which claimed benefit of U.S. provisional 61/375,367, filed Aug. 20, 2010, and U.S. provisional 61/375,189, filed Aug. 19, 2010. Each of the preceding applications is incorporated herein by reference.

The present invention concerns the synthesis of 5-methyl-2-furoic acid, including ester, amide, and thioester derivatives of such from 5-(chloromethyl)-2-furaldehyde (CMF). The molecules so prepared are useful as intermediates for pharmaceutical, food, and fragrance molecules; as well as fuel or fuel additives.

BACKGROUND ART

The generation of commodity chemicals from renewable feedstocks remains as one of the top priorities in the field of green chemistry. In addition, chemical processes that can operate in a catalytic fashion, such that toxic stoichiometric by-products can be avoided, will be essential in developing long-term, sustainable routes for molecules of interest. Though most catalytic processes in use today are mediated through the action of transition metals, recent advances have shown that certain all-organic scaffolds, i.e. containing only non-metal atoms such as carbon, hydrogen, nitrogen, sulfur, oxygen, or phosphorus, can act in a catalytic fashion and affect seemingly non-obvious transformations on reactive substrates.

Figure 2:
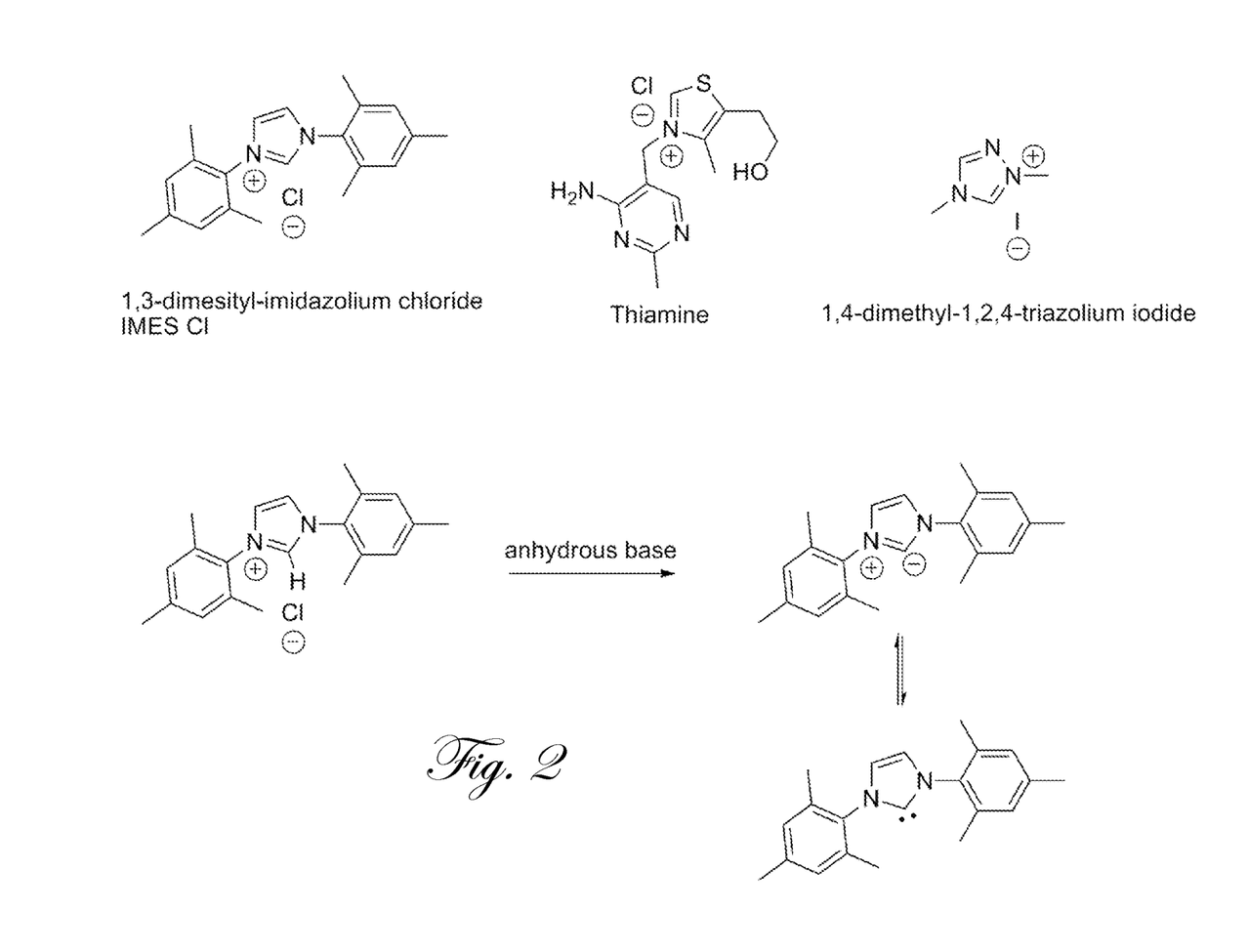
FIG. 2 illustrates the divergent reactivity of 5-(chloromethyl)-2-furaldehyde (CMF, 1) to either 5-(ethoxymethyl)-2-furaldehyde (EMF, 2) or ethyl 5-methyl-2-furoate (3) depending on the absence or presence of catalyst.

One such scaffold that is capable of unusual transformations comprise heterocyclic rings in which three consecutive atoms in the ring are of the form 'X$^+$=C$^-$—X', with 'X' being nitrogen, sulfur, silicon, or phosphorus (FIG. 2). Upon treatment with a suitable base, these molecules generate stabilized, singlet carbenes, containing a divalent carbon center. These carbenes are capable of imparting very unusual reactivity on certain organic functional groups; the most well understood being that of the vitamin Thiamine on pyruvate during metabolism. Much of the current academic research on these carbenes focuses on the grouping 'R(R')N$^+$=C—$^-$XR''', which have been termed 'N-heterocyclic carbenes (NHC)', and their action on aldehydes. Classically, aldehyde groups are considered to be highly reactive electrophiles, with a partial positive charge residing on the carbon atom. NHC organocatalysis is capable of reversing this charge, in a phenomenon known as 'umpolong' reactivity, wherein that same carbon now bears a partial negative charge in the aldehyde-NHC adduct (See Seebach *Angewandte Chemie International Edition in English* 18, 239 (1979)). The chemical literature contains examples of additions, eliminations, cycloadditions, and many other reactions where this intermediate is invoked.

Recent publications from Mark Mascal at the University of California, Davis, detailed a high yielding process from which 5-(chloromethyl)-2-furaldehyde (CMF) can be produced from a number of renewable cellulosic and hemicellulosic feedstocks (See Mascal and Nikitin *Energy & Fuels* 24, 2170 (2009)). As the process makes use of strong mineral acids, it is agnostic to stereochemistry and glycosidic linkages of the unit saccharides, and will convert six-carbon sugars to CMF, with the exception of deoxy sugars or gluconuric acids. Similar work in the field of furans-from-carbohydrates has focused on the generation of 5-(hydroxymethyl)-2-furaldehyde (HMF) (See Binder and Raines *Energy & Environmental Science* 3, 677 (2010)). Both CMF and HMF can be converted to valuable chemicals, primarily through catalytic hydrogenation to afford 5-methyl-2-furaldehyde or 2,5-dimethylfuran, or else oxidized to 2,5-furandicarboxylate, which can be used as a plastic monomer.

Figures 1, 3:
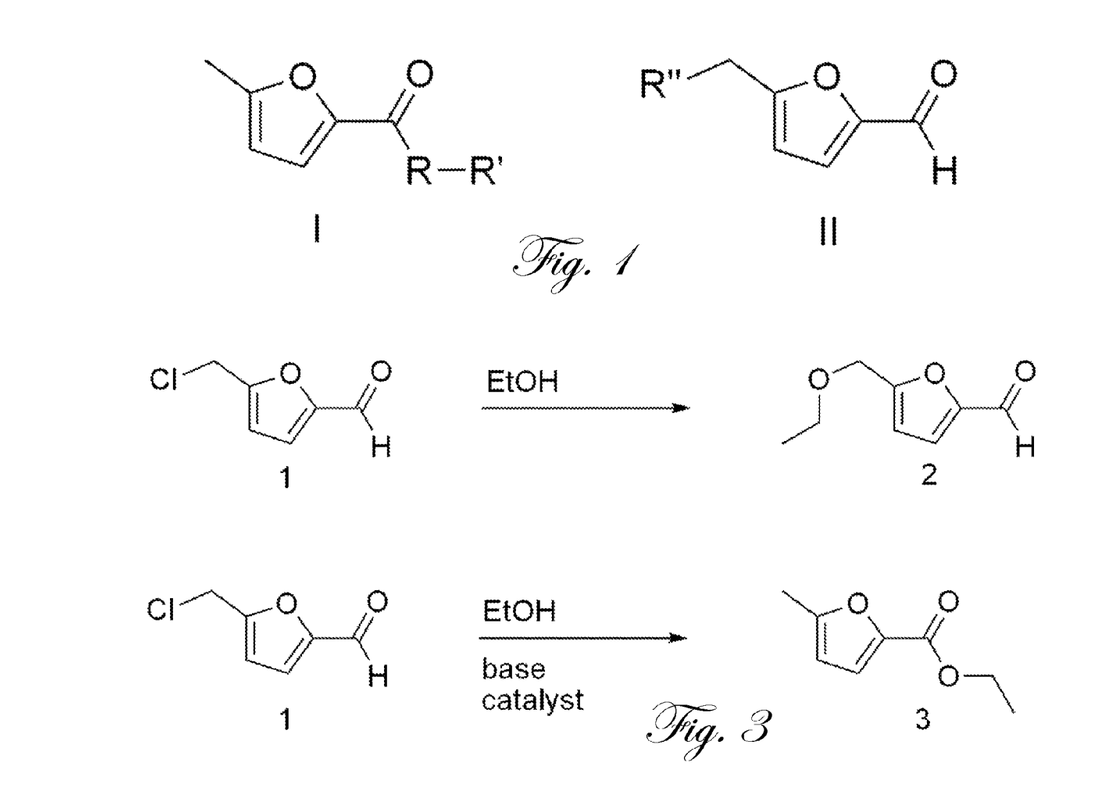
FIG. 1 illustrates molecules of formula I and formula II, which are the products and substrates, respectively, for the present invention.
FIG. 3 illustrates the proposed catalytic cycle mechanism of the present invention, along with that of known α-chloroaldehydes with NHC catalysis.
Figure 4:
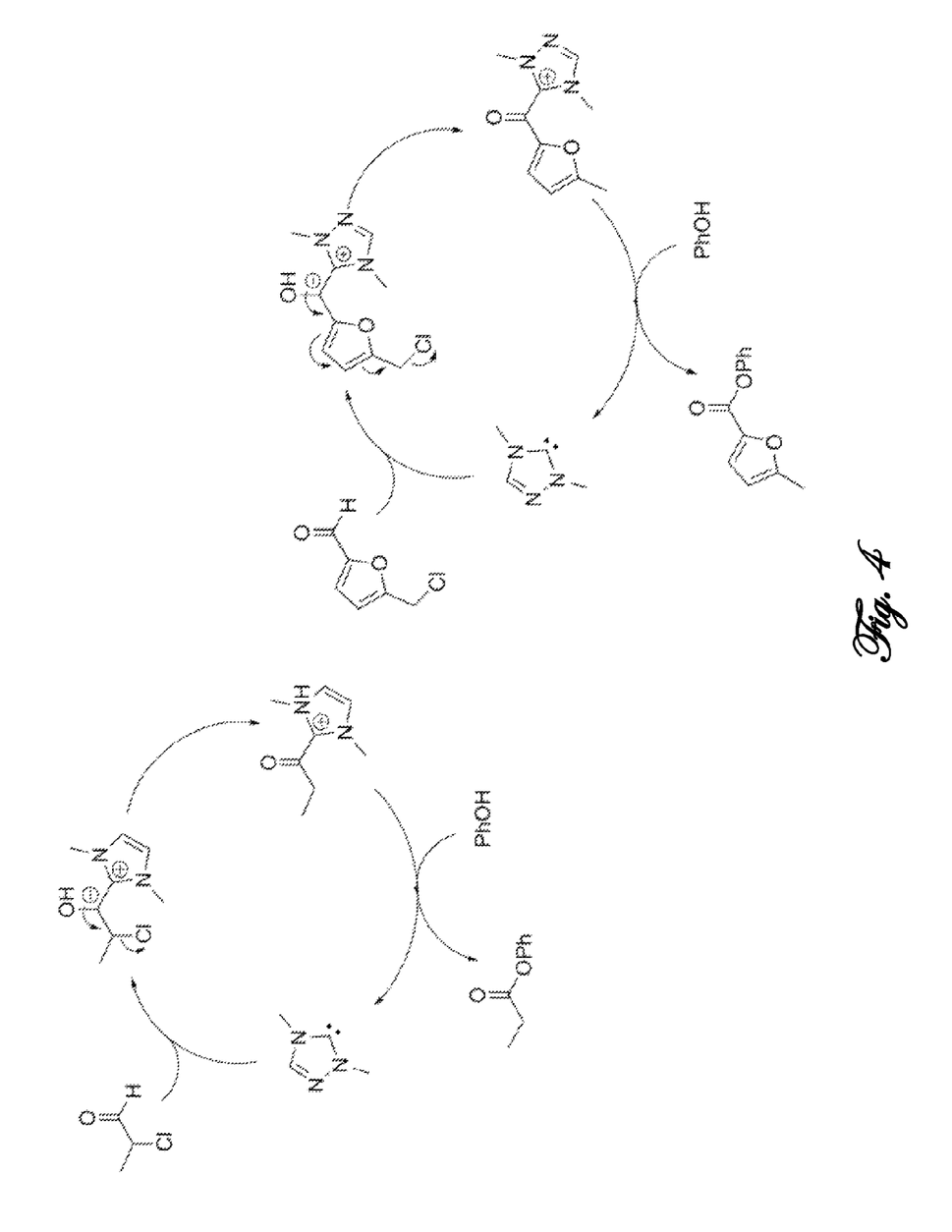
FIG. 4 illustrates representative precursor salts of N-heterocyclic carbene catalysts, and their deprotonation with bases.

Of particular relevance to the present invention is the conversion of CMF to 5-(ethoxymethyl)-2-furaldehyde (EMF) by Mascal (See Nikitin and Mascal *Angewandte Chemie International Edition* 47, 47 (2008)), which has demonstrated favorable fuel characteristics in terms of its energy content (30.3 MJ L-1). Though similar to gasoline in this regard, EMF failed to blend with gasoline at an appreciable level, and is also prone to auto-oxidation upon extended standing by virtue of the reactive aldehyde group (FIG. 3).

α-chloro-aldehydes are substrates that have been studied by Bode, Rovis, and Scheidt with NHC catalysis (See Sohn and Bode *Organic Letters* 7, 3873 (2005)); Reynolds and Rovis *Journal of the American Chemical Society* 127, 16406 (2005)); Chan and Scheidt *Organic Letters* 7, 905 (2005)). Mechanistically, after addition of the carbene to the aldehyde, the negative charge at the aldehyde-carbon center will eliminate chloride, affording an enol intermediate (FIG. 4). After tautomerization to the ketone, exogenous nucleophiles, such as alcohols, water, or amines, will expel the azolium moiety and regenerate the catalytic cycle. The resultant acid, ester, or amide, respectively, is immune from further reaction with the catalyst. CMF can be considered as a α-chloro-aldehyde, however the carbon-chlorine σ-bond is separated from the aldehyde π-bond by the furan ring system. In functional groups wherein a π-bond or π-system connects certain atoms, the group can be considered as 'vinylogous,' 'doubly-vinylogous,' etc. For example, an amide functional group with a carbon-carbon double bond connecting the nitrogen to the carbonyl is called a 'vinylogous amide.' In the case of CMF, the carbon-chlorine group and the aldehyde are 'doubly-vinylogous,' or perhaps, 'furanylogous,' where the furan π-system connects the bonds, and thus preserves the reactivity.

The present invention describes the high yielding conversion of CMF and related derivatives of 5-methyl-2-furaldehyde to 5-methyl-2-furoic acid and derivatives thereof using this novel transformation, catalyzed by NHC molecules. CMF, which is produced from renewable carbohydrate feedstocks, can be converted to useful products in a catalytic manner, without using transition metals, pressurized hydrogen gas, or extremes of pressure or temperature.

DESCRIPTION OF INVENTION

In one embodiment, the present invention provides a method for preparing methyl 5-methyl-2-furoate ester, in greater than 50% yield. The method includes contacting a furan-containing molecule of formula II, a base, an organic solvent, a catalyst, and methanol, at 32° C., such that methyl 5-methyl-2-furoate ester is produced.

In another embodiment, the present invention provides a method for preparing ethyl 5-methyl-2-furoate ester, in greater than 50% yield. The method includes contacting a furan-containing molecule of formula II, a base, an organic solvent, a catalyst, and ethanol, at 32° C., such that ethyl 5-methyl-2-furoate ester is produced.

MODES FOR CARRYING OUT THE INVENTION AND INDUSTRIAL APPLICABILITY

I. General

A method according to the present invention comprises preparing 5-methyl-2-furoic acid, including ester, amide and thioester derivatives from CMF, as useful chemical building blocks and fuel or fuel additives. The first step involves contacting a molecule of formula II, the catalyst, a base, an organic solvent and a reactive nucleophile, at temperatures between 10 degree C. and 50 degree C. The reaction is quenched with water, and hydrophobic furan product may be extracted with a hydrophobic solvent and purified by silica chromatography. The hydrophobic furan products may also be isolated by distillation, precipitation, or sublimation. The yield to methyl 5-methyl-2-furoate and ethyl 5-methyl-2-furoate are greater than 50% by this method. In the case of hydrophilic furan products, such as 5-methyl-2-furoic acid, the product may be purified by distillation, precipitation or sublimation.

II. Definitions

As used herein, the term "catalyst" refers to any atom or grouping of molecules that is present in sub-stoichiometric amounts with respect to the CMF, which is able to affect the desired chemical transformation to 5-methyl-2-furoic acid, and esters, amides, and thioesters thereof. The catalyst may also be present in equal or super-stoichiometric quantities with respect to CMF.

As used herein, the term "N-heterocyclic carbene" refers to any polycyclic or heterocyclic organic molecules, which contains at least two non-carbon atoms, which include one nitrogen, and one from the following: nitrogen, sulfur, phosphorus, or silicon; as well as at least one carbon atom. These atoms are arranged in such a way that upon treatment with an anhydrous base, a singlet carbene will form on a carbon atom contained within the heterocyclic ring.

As used herein, the term "nucleophile" refers to organic molecules that contain a reactive electronegative element. Examples include water; alcohols, including methanol, ethanol, butanol, propanol, and other aliphatic or aromatic groups; amines, including ammonia, alkyl ammonia, dialkyl ammonia, and trialkylammonia groups; and thiols, including hydrogen sulfide, and alkyl mercaptan species; and metal-stabilized carbon anions, such as alkyl-magnesium or alkyl-lithium species.

As used herein, the term "base" refers to molecules capable of neutralizing acidic species. Bases useful in the current invention include, but are not limited to, potassium carbonate, cesium carbonate, 1,8-diazabicyclo[5.4.0]undec-7-ene (DBU), 1,4-diazabicyclo[2.2.2]octane (DABCO), and quinuclidine. Other bases are also useful, such sodium carbonate, lithium carbonate, sodium bicarbonate, potassium bicarbonate, alkyl amines, dialkylamines, and trialkyl amines.

As used herein, the term "singlet carbene" refers to a carbon atom bonded to two substituents, with the remaining atomic orbital geometry comprising an s-orbital bearing two electrons, and an empty p-orbital.

As used herein, the term "organic solvent" refers to solvents which are generally non-polar, polar aprotic, or polar protic solvents. Organic solvents include, but are not limited to, tetrahydrofuran, acetonitrile, diethyl ether, methyl t-butyl ether, ethyl acetate, pentane, hexane, heptane, cyclohexane, benzene, toluene, methanol, ethanol, as well as halogenated solvents such as chloroform, dichloromethane, carbon tetrachloride, 1,2-dichloroethane, or combinations thereof. Other organic solvents are useful in the present invention.

As used herein, the term "hydrophobic solvent" refers to solvents which are immiscible with water. Extraction solvents include, but are not limited to, diethyl ether, ethyl acetate, methyl t-butyl ether, hexanes, pentane, heptane, cyclohexane, benzene, toluene, as well as halogenated solvents such as chloroform, dichloromethane, carbon tetrachloride, 1,2-dichloroethane, or combinations thereof. Other extraction solvents are useful in the present invention.

As used herein, the term "hydrophobic furan product" refers to products of this present process which contain a furan ring, and are generally insoluble with water. Hydrophobic furan products include, but are not limited to, aliphatic and aromatic esters of 5-methyl-2-furoic acid, aliphatic and aromatic amides of 5-methyl-2-furoic acid, and aliphatic and aromatic thioesters of 5-methyl-2-furoic acid. As used herein, the term "hydrophilic furan product" refers to products of this present process which contain a furan ring, and are generally soluble with water. Hydrophilic furan products include, but are not limited to, 5-methyl-2-furoic acid.

III. Method for Preparing 5-methyl-2-furoic Acid and Derivatives

The method of the present invention involves preparing furan-containing molecules of formula I, which are useful chemical building blocks and fuel or fuel additives, from furan-containing molecules of formula II, in greater than 50% yield. The first step involves contacting a furan-containing molecule of formula II, a base, such as DBU, an organic solvent, such as tetrahydrofuran (THF), a catalyst, such as an N-heterocyclic carbene, and a reactive nucleophile, such as alcohols, water, amines or thiols, in a reaction vessel at a temperature of from about −78 degree C. to 150 degree C. After completion, the second step involves separating the product molecules of formula I by extraction with a hydrophobic solvent, such as ethyl acetate. The yield to methyl 5-methyl-2-furoate and ethyl 5-methyl-2-furoate are greater than 70% by this method.

Useful products for the present invention include molecules of formula I, wherein R of formula I comprises oxygen, sulfur, and nitrogen; and wherein R' of formula I comprises carbon, hydrogen, sulfur, nitrogen, oxygen, or any aromatic or aliphatic combination thereof.

In some embodiments, the present invention provides a method for preparing 5-methyl-2-furoic acid. The method involves contacting furan-containing molecule of formula II, a base, an organic solvent, a catalyst, and water, in a reaction vessel at a temperature of from about −78 degree C. to 150 degree C.

In some embodiments, the present invention provides a method for preparing esters of 5-methyl-2-furoic acid. The method involves contacting furan-containing molecule of formula II, a base, an organic solvent, a catalyst, and an alcohol, such as methanol, ethanol, propanol, butanol, or other aliphatic or aromatic alcohol, in a reaction vessel at a temperature of from about −78 degree C. to 150 degree C.

In some embodiments, the present invention provides a method for preparing 5-methylfuran-2-carboxamide, or a substituted amide thereof. The method involves contacting furan-containing molecule of formula II, a base, an organic solvent, a catalyst, and an amine, such as ammonia, an aliphatic or aromatic alkylamine, or an aliphatic or aromatic dialkylamine, in a reaction vessel at a temperature of from about −78 degree C. to 150 degree C.

In some embodiments, the present invention provides a method for preparing 5-methylfuran-2-carbothioic S-acid, or an aliphatic or aromatic thioester thereof. The method involves contacting furan-containing molecule of formula II, a base, an organic solvent, a catalyst, and a thiol, such as hydrogen sulfide, or an aliphatic or aromatic thiol, in a reaction vessel at a temperature of from about −78 degree C. to 150 degree C.

The CMF used in the present invention comprises the exact molecular structure, "5-(chloromethyl)-2-furaldehyde", C6H5ClO2. CMF can be produced from carbohydrate-containing materials, such as agricultural, municipal or forestry waste streams. CMF can also be produced synthetically, from 5-methyl-2-furaldehyde, 5-(hydroxymethyl)-2-furaldehyde, or other furan derivatives through reactions known to those skilled in the art of organic synthesis.

Useful substrates for the present invention include molecules of formula II, including CMF, as well as other derivatives of 5-methyl-2-furaldehyde, wherein R'' of formula II comprises chloride, fluoride, bromide, iodide, p-toluenesulfonate, methanesulfonate, trifluoroacetate, phenoxy, hydroxy, ammonium, or other atoms or grouping of elements known to participate in this chemistry.

The catalyst used in the present invention comprises those atoms or groupings of atoms that are known to affect umpulong reactivity in aldehydes. For example, N-heterocyclic carbenes that contain any polycyclic or heterocyclic organic molecules containing one nitrogen atom, and at least one from the following: nitrogen, sulfur, phosphorus, or silicon; as well as at least one carbon atom. These atoms are arranged in such a way that upon treatment with an anhydrous base, a divalent carbon will form. Such examples include organic or inorganic salts of thiazolium, 1,2,4-triazolium, imidazolium, and tetrazolium ring systems, as well as other systems know to generate singlet carbenes. Still other useful catalysts include nucleophilic anion groups such as cyanide, chloride, bromide, and iodide.

The method of the present invention can be carried out at any suitable temperature. The temperature can be from −78 degree C. to 120 degree C. Other useful ranges for the temperature include from about 10 degree C. to about 50 degree C. Still other useful ranges for the temperature include from about 25 degree C. to about 35 degree C. One of skill in the art will appreciate that other temperature ranges are useful in the present invention.

Methods according to the present invention can be carried out over any suitable time duration. A useful time duration can be from 1 second to 24 hours. Other useful ranges include from about 1 hour to 4 hours. One of skill in the art will appreciate that other time durations are useful in the present invention.

An organic solvent used in the present invention comprises solvents which are miscible or immiscible with water. Organic solvents include, but are not limited to, tetrahydrofuran, acetonitrile, diethyl ether, methyl t-butyl ether, ethyl acetate, pentane, hexane, heptane, cyclohexane, benzene, toluene, methanol, ethanol, as well as halogenated solvents such as chloroform, dichloromethane, carbon tetrachloride, 1,2-dichloroethane, or combinations thereof. Other organic solvents are useful in the present invention.

A hydrophobic solvent in the present invention comprises a solvent that is immiscible with water. Extraction solvents include, but are not limited to, diethyl ether, ethyl acetate, methyl t-butyl ether, hexanes, pentane, heptane, cyclohexane, benzene, toluene, as well as halogenated solvents such as chloroform, dichloromethane, carbon tetrachloride, 1,2-dichloroethane, or combinations thereof. Other hydrophobic solvents are useful in the present invention.

A base used in the present invention can comprise an inorganic base. For example, the cation of the base can be an alkali metal, an alkaline earth metal, a transition metal, a post-transition metal, a lanthanide or an actinide. Alkali metals include Li, Na, K, Rb and Cs. Alkaline earth metals include Be, Mg, Ca, Sr and Ba. Transition metals include Sc, Ti, V, Cr, Mn, Fe, Co, Ni, Cu, Zn, Y, Zr, Nb, Mo, Tc, Ru, Rh, Pd, Ag, Cd, La, Hf, Ta, W, Re, Os, Ir, Pt, Au, Hg and Ac. The anion of the base can be carbonate, hydroxide, phosphate, sulfate, boronate, or acetate.

A base used in the present invention can also comprise a nitrogen-containing organic molecule. For example, any sp3 or sp2 hybridized amine, such as those contained in pyridine, triethylamine, diisopropylethylamine, trimethylamine, tripropylamine, tributylamine, N,N-dimethylaminopyridine, imidazole, or polycyclic amines, such as 1,8-diazabicyclo[5.4.0]undec-7-ene (DBU), 1,4-diazabicyclo[2.2.2]octane (DABCO), quinuclidine, quinoline, 1,5-diazabicyclo[4.3.0]non-5-ene (DBN), or other related bases.

A base can be present in any useful concentration in the present invention. For example, it can occur from super-stoichiometric quantities with respect to the moles of CMF, up to equimolar or sub-stoichiometric quantities.

A method of the present invention can also include other components and reagents known to one of skill in the art. For example, other components and reagents can include buffers, surfactants, additional salts, and additional solvents.

IV. Examples: Ethyl 5-methyl-2-furoate 1,3-dimesityl-1H-imidazol-3-ium iodide (0.031 g, 0.138 mmol) was suspended in tetrahydrofuran (46 ml) and ethanol (16.2 ml). 1,8-diazabicyclo[5.4.0]undec-7-ene (4.14 ml, 27.68 mmol) was then added and the reaction heated to 32° C. CMF (2.00 g, 13.84 mmol) was dissolved in THF (8 ml), and added dropwise over the course of 60 minutes. Stirring was continued for an additional 2 hours, during which time the reaction took on a deep red color. Water (100 ml) was then added, and the reaction extracted with ethyl acetate (3×150 ml). The combined organic extracts were pooled and washed with brine. Desiccation over $Na_2SO_4$ and solvent evacuation preceded silica chromatography of the residue (15% Ethyl Acetate:Hexanes), which furnished the ester as a pale yellow oil (1.56 g, 73% yield): 1HNMR δ (CDCl3): 7.04 (d, 1H, J=3 Hz), 6.07 (d, 1H, J=3 Hz), 4.31 (q, 1H, J=7 Hz), 2.34 (s, 3H), 1.33 (t, 2H, J=7 Hz); 13CNMR δ (CDCl3): 158.79, 156.97, 143.18, 119.13, 108.29, 60.60, 14.29, 13.89.

Other Embodiments

Glycerol is a three-carbon poly-hydroxylated organic molecule that is produced in abundance by all living organisms. It serves as the backbone for triacylglycerides, which are the primary source of cellular energy derived from fats, as well as for phospholipids, which comprise the lipid bilayer of cellular membranes. Glycerol's low toxicity and inherent "sweet" taste has seen its inclusion into low calorie foods as a glucose substitute. As a three-carbon, prochiral synthon, glycerol has been utilized as a starting material for many pharmaceutical compounds, as well as academic chemical methodologies. In recent years, the worldwide supply of glycerol has increased dramatically as the demand for biodiesel fuel rises, and it is projected that 1.2 million tons of glycerol will be generated in 2010. See, e.g., Ott, L. Bicker, M.; Vogel, H. Green Chem. 2006, 8, 214, which is incorporated herein by reference. Triacylglycerols (triglycerides) are typically harvested from plant and algal material, then transesterified with short aliphatic alcohols to liberate the fatty acids from the glycerol core. These fatty ester products display ideal diesel fuel characteristics, however due to its high water solubility and poor flammability, glycerol is seen as an unwanted by-product in this industry.

Figure 5:
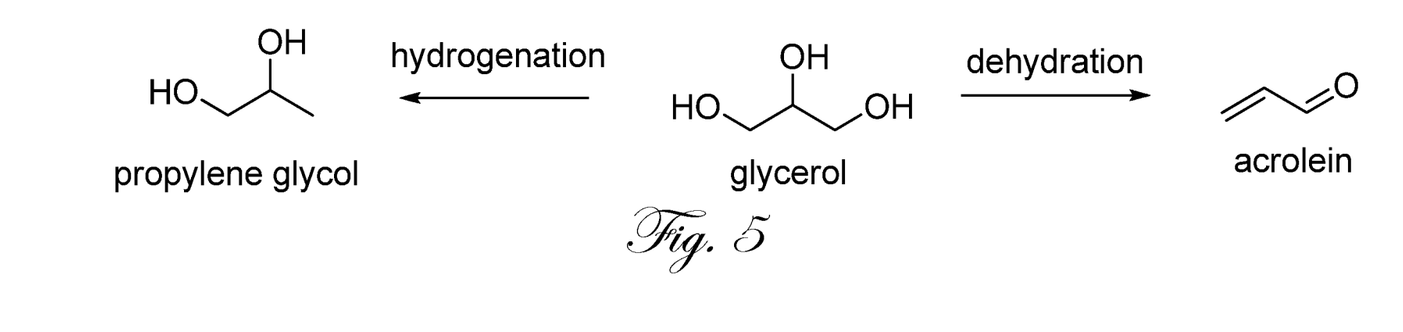
FIG. 5 is a schematic illustration of the reduction of glycerol to 1,2-propanediol, or dehydration to acrolein.

A number of chemical methods for the conversion of glycerol to commodity chemicals have been examined. Many involve the further oxidation of glycerol to acrylate derivatives, which have found use in the polymer industry. The reduction of glycerol to 1,2- or 1,3-propanediol can be accomplished using various platinum group metals and hydrogen gas at elevated temperatures (see FIG. 5). One particular method involves the catalytic dehydration of glycerol to acrolein. See, e.g., Katryniok, B.; Paul, S.; Capron, M.; Dumeignil, F. ChemSusChem, 2009, 2, 719-730, which is incorporated herein by reference. While not a potential fuel itself, this process is capable of removing two oxygens from glycerol through non-hydrogenative conditions, and it is our supposition that acrolein can be combined with other short-chain molecules to generate fuels or chemicals of interest.

Chemically, acrolein contains an aldehyde group and an alkene group. As such, acrolein is highly electrophilic and prone to polymerization, so it is used quickly after generation from glycerol. Limiting the acrolein polymerization to controlled dimerization and trimerization can afford six-carbon and nine-carbon molecules, respectively, which contain low oxygen to carbon ratios, and can fall into the proper fuel specifications for transportation or aviation fuel. Example embodiments of the present invention provide a method for generating a dimerized product of acrolein through the use of N-heterocyclic carbene (NHC) catalysis.

Figure 6:
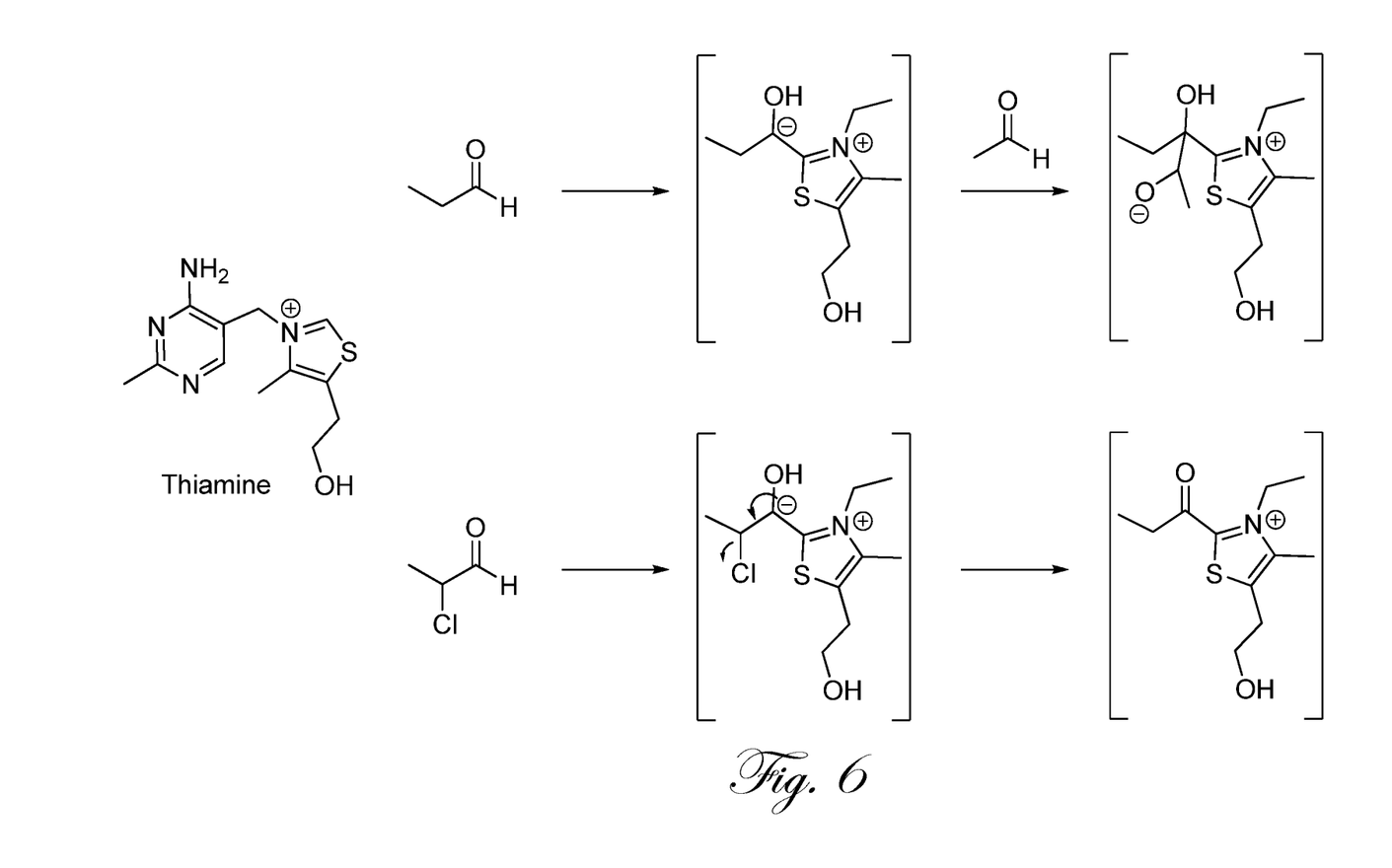
FIG. 6 is a schematic illustration of thiazolium or triazolium ring systems as nucleophilic agents.

NHC catalysts take advantage of unusual chemical behaviors of carbenes, which have been known to impart inverted reactivity on certain substrates, i.e., "umpulong" reactivity, such as nucleophilic acyl groups. See, e.g, Seebach, D. Angew. Chem. Int. Ed. 1979, 18, 239-258, which is incorporated herein by reference; Breslow, R. J. Am. Chem. Soc. 1958, 80, 3719-3726, which is incorporated herein by reference. So-called "persistent" carbenes are encountered in nature in the form of vitamin B1, thiamine, which is involved in pyruvate decarboxylation and the subsequent use of the chemical intermediate in cellular metabolism. Recent work by Rovis, Bode, and Scheidt has expanded the scope of this catalyst to include a multitude of α-oxoacids and aldehydes in reactions that otherwise could not occur under conventional catalysis. See, e.g., Reynolds, N. T.; de Alaniz, J. R.; Rovis, T. J. Am. Chem. Soc. 2004, 126, 9518-9519, which is incorporated herein by reference; Chan, A.; Scheidt, K. A. Org. Lett. 2005, 7, 905-908, which is incorporated herein by reference; Chow, K. Y.-K.; Bode, J. J. Am. Chem. Soc. 2004, 126, 8126-8127, which is incorporated herein by reference. Under basic conditions, the thiazolium, imidazolium, or triazolium ring systems act as nucleophilic agents, and will attack electron-deficient carbonyl centers (see FIG. 6). After proton transfer, the acyl carbon center has in turn become nucleophilic and will attack nearby electrophiles, or transfer these electrons to an internal, proximal nucleofuge and effectively create an "internal redox".

Figure 7:
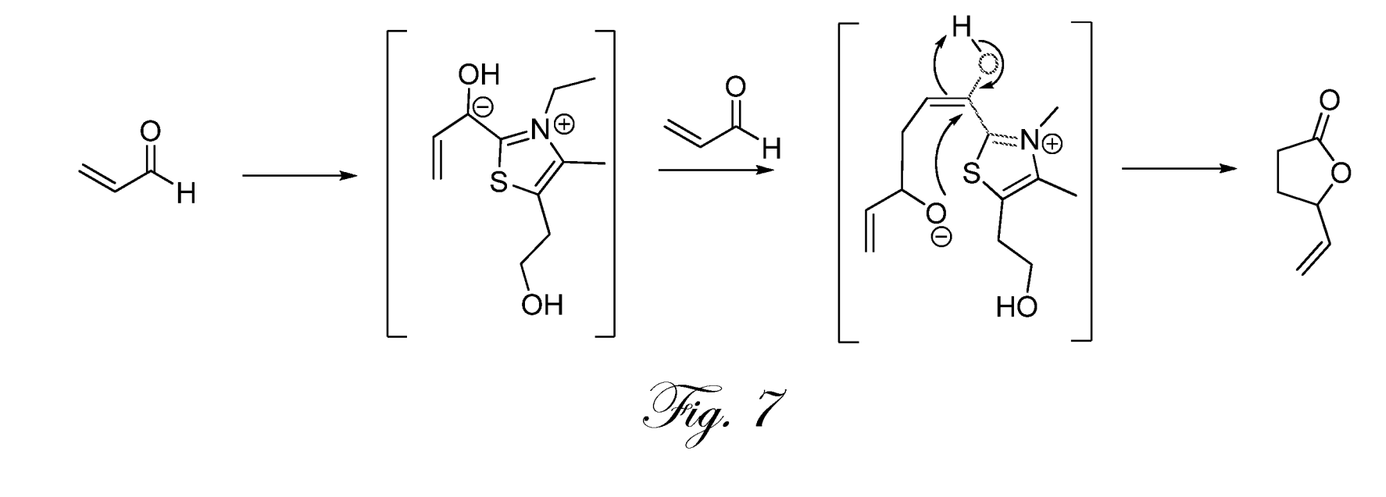
FIG. 7 is a schematic illustration of an example method according to the present invention.

As contemplated in the present invention, two molecules of acrolein can afford the 5-vinylbutyrolactone product shown in FIG. 7, through a NHC cascade reaction, using vitamine B1, or other heterocyclic moiety capable of similar catalysis. Glorius and Bode have shown a transformation of a similar type, wherein a putative homoenolate of an enal can be generated via NHC catalysis, followed by intermolecular attack onto an aldehyde, followed by ring closure and expulsion of catalyst. See, e.g., Sohn, S. S.; Rosen, E. L.; Bode, J. W. J. Am. Chem. Soc. 2004, 126, 14370-14371, which is incorporated herein by reference; Burstein, C.; Glorius, F. Angew. Chem. Int. Ed. 2004, 43, 6205-6208, which is incorporated herein by reference.

Figure 8:
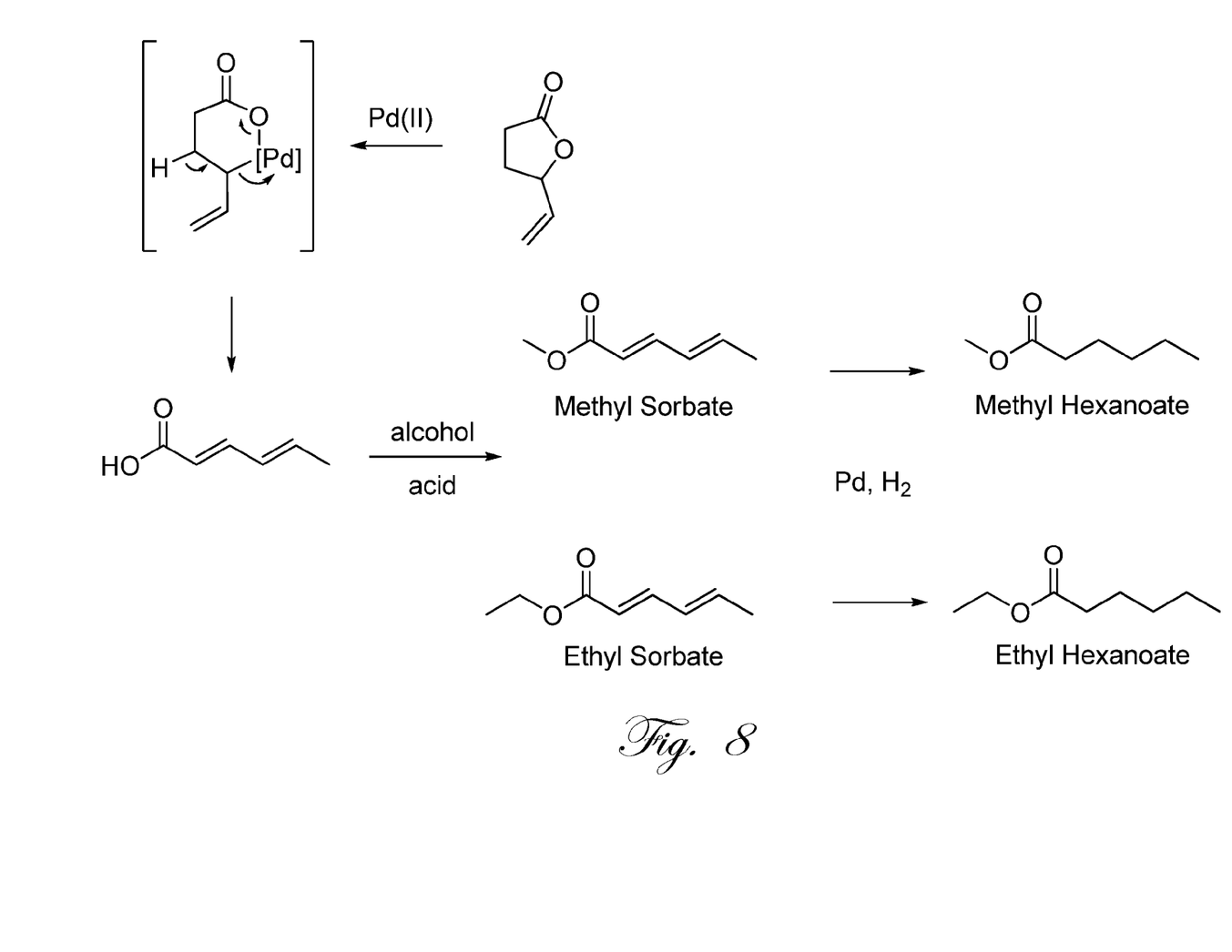
FIG. 8 is a schematic illustration of an example method according to the present invention.

In this intermediate is contained an allylic acetate, which will be susceptible to $Pd(II)Cl_2$ insertion. Rearrangement to the e-lactone is highly disfavored entropically, so β-hydride elimination will occur followed by olefin isomerization to afford sorbic acid, a six-carbon commodity chemical, which is widely used in the food industry as a preservative. Esterification of sorbic acid with methanol or ethanol under acid catalysis will generate methyl sorbate and ethyl sorbate, respectively, which display similar melting points and flash points to aviation fuels (flash point: 63° C. and 69° C., respectively; melting point: −46° C. and −34° C., respectively). Hydrogenation of these compounds will provide methyl and ethyl hexanoate derivatives, which show even lower values for the above fuel categories (flash point: 45° C. and 49° C., respectively; melting point: −71° C. and −67° C., respectively). FIG. 8 is a schematic illustration of the above process.

An example embodiment according to the present invention provides a method for the conversion of glycerol to a liquid fuel comprising: catalytic dehydration of glycerol to acrolein; controlled condensation of acrolein to 5-vinylbutyrolactone; conversion of 5-vinylbutyrolactone to sorbic acid; esterification of sorbic acid to a sorbate ester; and hydrogenation of the sorbate ester to a hexanoate ester. In such a method, the catalytic dehydration of glycerol to acrolein can comprise reaction with one or more of potassium bisulfate, sulfuric acid, phosphoric acid, magnesium sulfate, zinc sulfate or aluminum sulfate. In such a method, the catalytic dehydration of glycerol to acrolein can be performed at temperatures between 473 kelvin and 673 kelvin, and can be performed in batch processes and in continuous processes or combinations thereof.

The controlled condensation of acrolein to 5-vinylbutyrolactone can comprise reaction with catalytic systems that affect inverted reactivity on acyl groups, such that they become nucleophilic. In such an embodiment, the catalytic systems can comprise one or more of thiazolium, triazolium, or imidazolium ring systems.

The conversion of 5-vinylbutyrolactone to sorbic acid can comprise isomerization by palladium. The esterification of sorbic acid to a sorbate ester can comprises acid catalyzed esterification with an alcohol. The esterification of sorbic acid to a sorbate ester can comprise conversion of the acid to an acid chloride or mixed anhydride or carbonate and reaction with an alcohol. The esterification of sorbic acid to a sorbate ester can comprise activation of the acid by a carbodiimide coupling agent or other dehydrating reagent and reaction with an alcohol. The hydrogenation of a sorbate ester to a hexanoate ester can comprise reduction by a noble metal, such as palladium, platinum, rhodium, iridium, nickel, iron, or ruthenium, under elevated pressures of hydrogen gas.

Example embodiments of the present invention comprise liquid fuels produced by any of the methods described herein. Example embodiments of the present invention comprise apparatuses for the performance of any of the methods described herein.

Other Embodiments

The catalytic deoxygenation of cellulosic material is a significant hurdle in the development of cost-effective energy dense liquid fuels. The direct reduction of a carbon-hydroxyl bond is heavily disfavored thermodynamically, and current state-of-the-art technologies for doing so involve high temperatures, high pressures of hydrogen gas, as well as a platinum-group metal catalyst system for group activation. Nature has circumvented this problem by capping these hydroxyls as phosphate groups, followed by elimination to provide the olefin. There are numerous deoxygenation protocols in the organic synthesis literature, though none of these will be compatible in an aqueous environment, nor will they be free of by-products, of which many can be of higher molecular weight than the starting glucose molecule.

Recent reports by Zhang and Raines have shown that cellulosic material can be dehydrated through several steps to form furan-based products. See, e.g., Su, Y.; Brown, H. M.; Huang, W.; Zhou, X.-d.; Amonette, J. E.; Zhang, C. "Single-step Conversion of Cellulose to 5-hydroxymethylfurfural (HMF), a Versatile Platform Chemical." App. Cat. A: General. 2009, 361, 117-122, incorporated herein by reference; Binder, J. B.; Raines, R. T. "Simple Chemical Transformation of Lignocellulosic Biomass into Furanics for Fuels and Chemicals." J. Am. Chem. Soc. 2009, 131, 1979-1985, incorporated herein by reference. Small scale reactions have shown that glucose can be converted to fructose using chromium catalysis in a dry ionic liquid solvent, followed by dehydration to hydroxymethylfurfural (HMF). This reaction proceeds in good overall yield, however the reaction conditions are not amenable to large scale production.

A report by Mascal has addressed these issues and developed an acid catalyzed procedure for the production of 5-(chloromethyl)furfural (CMF) from cellulose directly. See, e.g., Mascal, M.; Nikitin, E. B.; "Direct, High-Yield Conversion of Cellulose into Biofuel." Angew. Chem. Int. Ed. 2008, 47, 7924-7926, incorporated herein by reference. Using acid, heat, lithium chloride, and a biphasic reaction setup, hydrophobic CMF can be continuously extracted from the reaction medium and then utilized for subsequent etherification or condensation reactions. The present invention provides a novel chemical transformation on CMF, involving an oxidative coupling reaction to generate furoate esters which may serve as "drop-in" gasoline or diesel fuel surrogates.

α-chloroaldehydes have been shown to undergo an internal oxidation-reduction reaction to generate ester products when treated with thiamine-like (Vitamin B1) molecules. See, e.g., Reynolds, N. T.; de Alaniz, J. R.; Rovis, T. "Conversion of α-haloaldehydes into acyating agents by an internal redox reaction catalyzed by nucleophilic carbenes." J. Am. Chem. Soc. 2004, 126, 9518-9519, incorporated herein by reference. CMF does not contain a α-chloroaldehyde per se; however the aromatic connection between the aldehyde and chloromethyl links these groups through conjugative effects, and can therefore be thought of as a "doubly-vinylogous or phenylic" α-chloroaldehyde. There have been no reports of a reaction of this kind.

Figure 9:
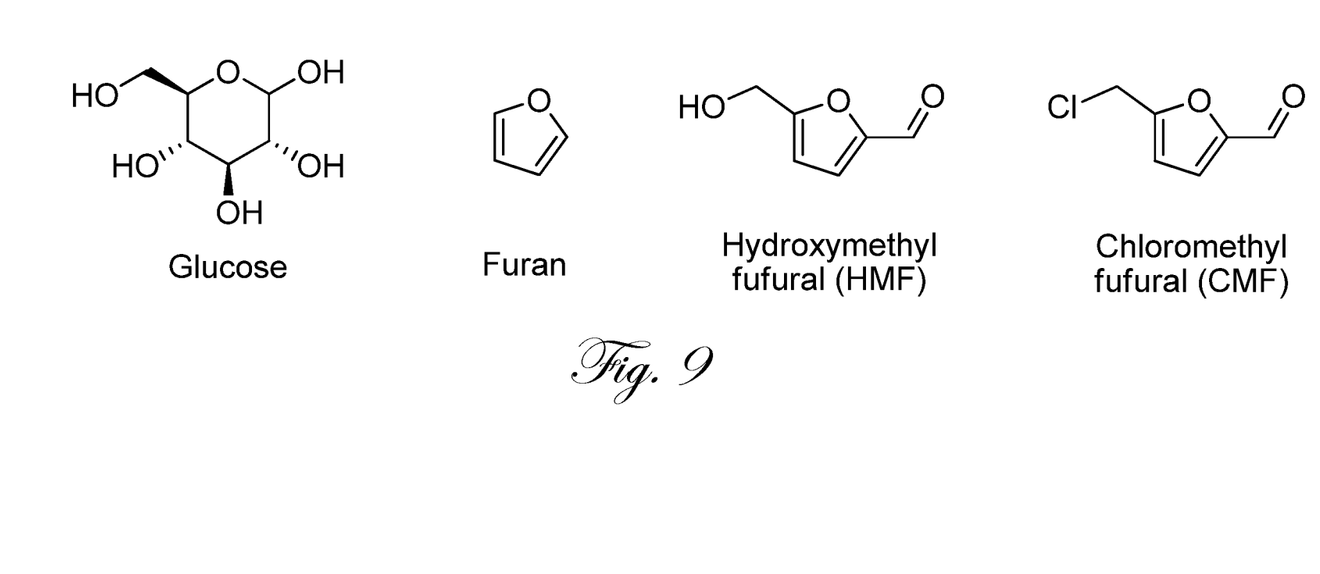
FIG. 9 is a schematic illustration of glucose and derived molecules.
Figure 10:
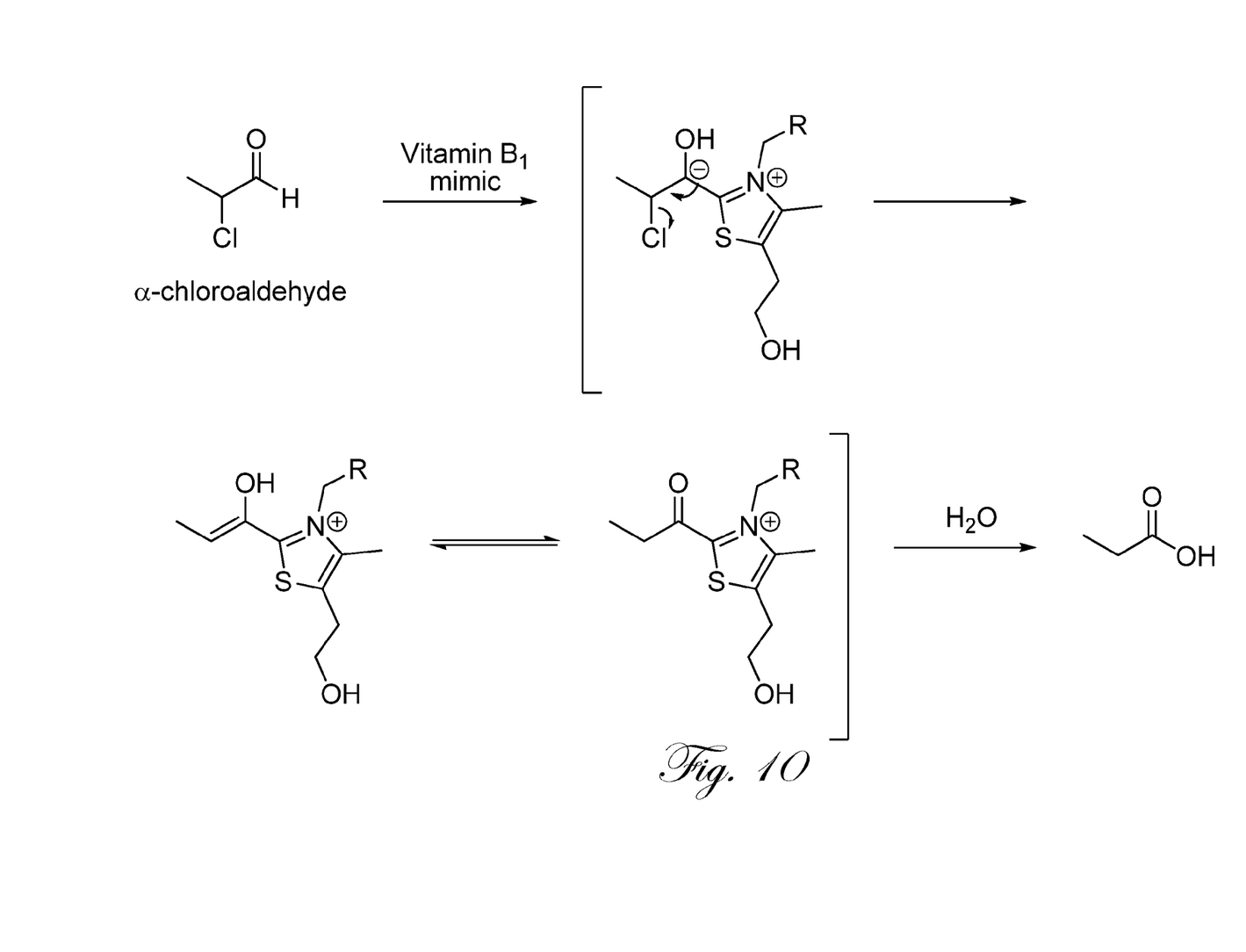
FIG. 10 is a schematic illustration of chloroaldehyde attacked by the thiazolium ring, followed by elimination of the chloride. Tautomerization to the ketone provides an intermediate which is susceptible to hydrolysis.
Figure 11:
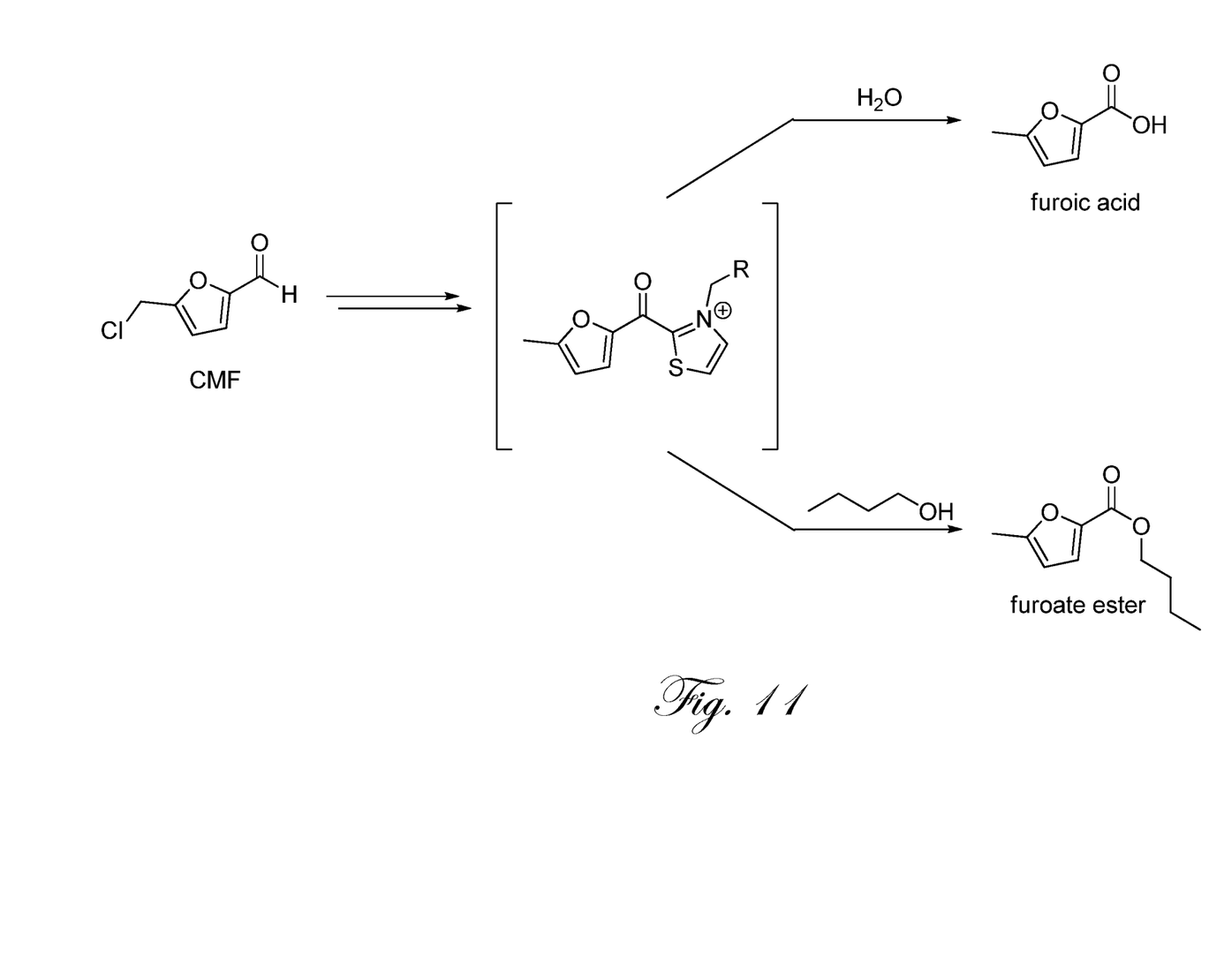
FIG. 11 is a schematic illustration of disparate reactivity of the acyl intermediate to provide furoate esters.

FIG. 9 illustrates schematically chloroaldehyde attacked by the thiazolium ring, followed by elimination of the chloride. Tautomerization to the ketone provides an intermediate which is susceptible to hydrolysis by water or esterification by an alcohol.

To facilitate catalyst recovery, thiazolium of triazolium hetereocycle can be attached to a solid support or supramolecular construct, such as a calixarene or cyclodextrin molecule. Breslow has shown that thiazolium salts covalently anchored to γ-cyclodextrin operate nine times faster than their free counterparts in the analogous benzoin condensation. Breslow, R.; Kool, E. "A γ-Cyclodextrin Thiazolium Salt Holoenzyme Mimic for the Benzoin Condensation." Tetrahedron Lett. 1988, 29, 1635-1638, incorporated herein by reference.

An example embodiment according to the present invention provides a method for the conversion of 5-(chloromethyl)furfural to a liquid fuel comprising: nucleophilic addition of a carbene catalyst to the aldehyde of 5-(chloromethyl)furfural and loss of chloride ion; displacement of the carbene catalyst with an alcohol. In such a method, the carbene catalyst can comprise a thiazolium, triazolium or imidazolium heterocycle. In such a method, the reaction solvent can comprise an appropriately buffered aqueous solution, or organic solvent, such as dichloromethane, dimethylformamide, tetrahydrofuran, chloroform, benzene, toluene, or acetonitrile.

The displacement of the carbene catalyst with an alcohol can comprise reaction with any aliphatic or aromatic alcohol, such that a furoate ester product is generated.

Although the foregoing invention has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference.

We claim:

1. A method for the synthesis of an output consisting of one or more of: an ester of 5-methyl-2-furoic acid, an amide of 5-methyl-2-furoic acid, and a thioester of 5-methyl-2-furoic acid, from a precursor consisting of 5-methyl-furaldehyde with one hydrogen of the 5-methyl group replaced with one of chloride, fluoride, bromide, iodide, p-toluenesulfonate, methanesulfonate, trifluoroacetate, phenoxy, hydroxy, or ammonium, the method comprising: (a) contacting the precursor, a base, an organic solvent, a catalyst, and a reactive nucleophile in a reaction vessel at a temperature of from about 35 degrees C. to about 50 degrees C., such that molecules of the output are produced; (b) separating the molecules of the output by extraction with a hydrophobic solvent, or else by chromatography, distillation, sublimation, or precipitation; wherein the catalyst is one or more of: (1) a N-heterocyclic carbene, (2) a salt of a N-heterocyclic carbene, (3) cyanide, (4) chloride, (5) bromide, (6) iodide, (7) thiazolium, (8) 1,2,4-triazolium, (9) imidazolium, (10) tetrazolium ring system.

2. A method as in claim 1, wherein the output is an ester of 5-methyl-2-furoic acid having an alkoxycarbonyl portion, and wherein the alkoxycarbonyl portion is linear or branched aliphatic chain or a cyclic aliphatic, having at least 1 and not more than 20 carbon atoms.

3. A method as in claim 1, wherein the output is an ester of 5-methyl-2-furoic acid having an aryloxycarbonyl portion, and wherein the aryloxycarbonyl portion is an aromatic ring, having at least 5 and not more than 10 carbon atoms.

4. A method as in claim 1, wherein the reactive nucleophile is an alcohol.

5. A method as in claim 1, wherein the reactive nucleophile is an amine.

6. A method as in claim 1, wherein the reactive nucleophile is a thiol.

7. A method as in claim 1, wherein the hydrophobic solvent comprises a solvent that is immiscible with water.

8. A method for the synthesis of an output consisting of one or more of: an ester of 5-methyl-2-furoic acid, an amide of 5-methyl-2-furoic acid, and a thioester of 5-methyl-2-furoic acid, from a precursor consisting of 5-methyl-furaldehyde with one hydrogen of the 5-methyl group replaced with one of chloride, fluoride, bromide, iodide, p-toluenesulfonate, methanesulfonate, trifluoroacetate, phenoxy, hydroxy, or ammonium, the method comprising: (a) contacting the precursor, a base, an organic solvent, a catalyst, and a silanol in a reaction vessel at a temperature of from about −78 degrees C. to about 150 degrees C., such that molecules of the output are produced; (b) separating the molecules of the output by extraction with a hydrophobic solvent, or else by chromatography, distillation, sublimation, or precipitation; wherein the catalyst is one or more of: (1) a N-heterocyclic carbene, (2) a salt of a N-heterocyclic carbene, (3) cyanide, (4) chloride, (5) bromide, (6) iodide, (7) thiazolium, (8) 1,2,4-triazolium, (9) imidazolium, (10) tetrazolium ring system.

9. A method as in claim 8, wherein the output is an ester of 5-methyl-2-furoic acid having an alkoxycarbonyl portion, and wherein the alkoxycarbonyl portion is linear or branched aliphatic chain or a cyclic aliphatic, having at least 1 and not more than 20 carbon atoms.

10. A method as in claim 8, wherein the output is an ester of 5-methyl-2-furoic acid having an aryloxycarbonyl portion, and wherein the aryloxycarbonyl portion is an aromatic ring, having at least 5 and not more than 10 carbon atoms.

11. A method as in claim 8, wherein the base comprises an inorganic base.

12. A method as in claim 8, wherein the base comprises a nitrogen-containing organic base.

13. A method as in claim 8, wherein the hydrophobic solvent comprises a solvent that is immiscible with water.

* * * * *